US009598341B2

(12) United States Patent
Mullen et al.

(10) Patent No.: US 9,598,341 B2
(45) Date of Patent: *Mar. 21, 2017

(54) PROCESS TO PREPARE LEVULINIC ACID

(71) Applicant: GFBiochemicals Limited, Valletta (MT)

(72) Inventors: Brian D. Mullen, Delano, MN (US); Dorie Janine Yontz, Bloomington, MN (US); Cora M. Leibig, Maple Grove, MN (US)

(73) Assignee: GFBiochemicals Limited, Valletta (MT)

( * ) Notice: Subject to any disclaimer, the term of this patent is extended or adjusted under 35 U.S.C. 154(b) by 0 days.

This patent is subject to a terminal disclaimer.

(21) Appl. No.: 14/748,278

(22) Filed: Jun. 24, 2015

(65) Prior Publication Data

US 2015/0291499 A1    Oct. 15, 2015

Related U.S. Application Data

(63) Continuation of application No. 13/831,317, filed on Mar. 14, 2013, now Pat. No. 9,073,841.

(60) Provisional application No. 61/722,766, filed on Nov. 5, 2012.

(51) Int. Cl.
C07C 59/00 (2006.01)
C07C 51/00 (2006.01)

(52) U.S. Cl.
CPC .................... C07C 51/00 (2013.01)

(58) Field of Classification Search
CPC .............................. C07C 51/00; C07C 59/185
See application file for complete search history.

(56) References Cited

U.S. PATENT DOCUMENTS

| 1,861,200 | A | 5/1932 | Webber et al. |
|---|---|---|---|
| 2,008,720 | A | 7/1935 | Lawson et al. |
| 2,029,412 | A | 2/1936 | Cox et al. |
| 2,040,849 | A | 5/1936 | Holt |
| 2,257,389 | A | 9/1941 | Macallum |
| 2,270,328 | A | 1/1942 | Moyer |
| 2,293,724 | A | 8/1942 | Faerber |
| 2,305,738 | A | 12/1942 | Scheuing et al. |
| 2,382,572 | A | 8/1945 | Meyer |
| 2,684,981 | A | 7/1954 | Sherman |
| 2,738,367 | A | 3/1956 | Redmon |
| 2,780,588 | A | 2/1957 | Dunlop |
| 2,813,900 | A | 11/1957 | Dunlop et al. |
| 2,840,605 | A | 6/1958 | Leonard |
| 2,917,537 | A | 12/1959 | Haury |
| 3,065,263 | A | 11/1962 | Carlson |
| 3,258,481 | A | 6/1966 | Sassenrath et al. |
| 3,267,136 | A | 8/1966 | Vincenty et al. |
| 3,275,505 | A | 9/1966 | Herschler et al. |
| 3,580,906 | A | 5/1971 | Bernasek |
| 3,663,612 | A | 5/1972 | Ramos-Rodriguez |
| 3,701,789 | A | 10/1972 | Ramos-Rodriguez |
| 4,236,021 | A | 11/1980 | Hsu et al. |
| 4,342,831 | A | 8/1982 | Faber et al. |
| 4,590,283 | A | 5/1986 | Gaset et al. |
| 4,615,742 | A | 10/1986 | Wright |
| 5,175,358 | A | 12/1992 | Capai et al. |
| 5,188,673 | A | 2/1993 | Clausen et al. |
| 5,859,263 | A | 1/1999 | Ghorpade et al. |
| 5,892,107 | A | 4/1999 | Farone et al. |
| 6,054,611 | A * | 4/2000 | Farone ................... C07C 51/00 549/429 |
| 7,317,116 | B2 | 1/2008 | Sanborn |
| 7,393,963 | B2 | 7/2008 | Sanborn et al. |
| 7,432,382 | B2 | 10/2008 | Sanborn et al. |
| 7,520,905 | B1 | 4/2009 | Lightner |
| 7,579,489 | B2 | 8/2009 | Sanborn |
| 7,579,490 | B2 | 8/2009 | Sanborn et al. |
| 7,829,732 | B2 | 11/2010 | Mascal |
| 7,939,681 | B2 | 5/2011 | Zhao et al. |
| 7,959,765 | B2 | 6/2011 | Argyropoulos |
| 8,058,458 | B2 | 11/2011 | Sanborn |
| 8,115,020 | B2 | 2/2012 | Sanborn |
| 9,073,841 | B2 * | 7/2015 | Mullen ................... C07C 51/00 |
| 2008/0241902 | A1 | 10/2008 | Berry et al. |
| 2008/0311637 | A1 | 12/2008 | Navapanich et al. |
| 2009/0156841 | A1 | 6/2009 | Sanborn et al. |
| 2009/0234142 | A1 | 9/2009 | Mascal |
| 2010/0024806 | A1 | 2/2010 | Burke et al. |
| 2010/0024807 | A1 | 2/2010 | Burke et al. |
| 2010/0024808 | A1 | 2/2010 | Burke et al. |
| 2010/0024809 | A1 | 2/2010 | Burke et al. |

(Continued)

FOREIGN PATENT DOCUMENTS

AU    2011/205116    8/2011
AU    2011/205117    8/2011

(Continued)

OTHER PUBLICATIONS

MIT Jan. 2012, four pages 61-63 and the fourth page is not numbered.*

Aida, et al. "Dehydration of d-glucose in high temperature water at pressures up to 80MPa", J. of Supercritical Fluids, No. 40, 2007, pp. 381-388.

Assary, et al., "Computational Studies of the Thermochemistry for Conversion of Glucose to Levulinic Acid", J. Phys. Chem. B. No. 114, 2010, pp. 9002-9009.

Bart, et al., "Kinetics of Esterification of Levulinic Acid With N-Butanol by Homogeneous Catalysis", Ind. Eng. Chem. Res. No. 33, 1994, pp. 21-25.

Baugh, et al., "Thermochemical Pretreatment of Lignocellulose to Enhance Methane Fermentation: I. Monosaccharide and Furfurals Hydrothermal Decomposition and Product Formation Rates", Biotechnology and Bioengineering, vol. 31, 1988, pp. 50-61.

(Continued)

*Primary Examiner* — Yevegeny Valenrod
*Assistant Examiner* — Blaine G Doletski
(74) *Attorney, Agent, or Firm* — Todd K. Macklin; Norton Rose Fulbright US LLP

(57) ABSTRACT

The invention describes processes to prepare levulinic acid, formic acid and/or hydroxymethyl furfural from various biomass materials.

16 Claims, No Drawings

(56) References Cited

U.S. PATENT DOCUMENTS

| | | | |
|---|---|---|---|
| 2010/0028089 A1 | 2/2010 | Burke et al. | |
| 2010/0044210 A1 | 2/2010 | Robinson | |
| 2010/0186735 A1 | 7/2010 | Burke et al. | |
| 2010/0186736 A1 | 7/2010 | Burke et al. | |
| 2010/0284900 A1 | 11/2010 | Chen | |
| 2010/0312006 A1 | 12/2010 | Lake et al. | |
| 2010/0324310 A1 | 12/2010 | Dumesic et al. | |
| 2011/0011391 A1 | 1/2011 | Burke et al. | |
| 2011/0071306 A1 | 3/2011 | Robinson | |
| 2011/0105770 A1 | 5/2011 | Liu et al. | |
| 2011/0144396 A1 | 6/2011 | Lotero et al. | |
| 2011/0207922 A1 | 8/2011 | Kubo et al. | |
| 2012/0302764 A1* | 11/2012 | Dumesic | C07C 51/48 549/326 |

FOREIGN PATENT DOCUMENTS

| | | |
|---|---|---|
| AU | 2011/205118 | 8/2011 |
| CN | 1680257 | 10/2005 |
| CN | 101148458 | 3/2008 |
| CN | 101381351 | 3/2009 |
| CN | 101648863 | 2/2010 |
| CN | 101691326 | 4/2010 |
| CN | 101781210 | 7/2010 |
| CN | 102093206 | 6/2011 |
| DE | 3621517 | 1/1988 |
| EP | 1860201 | 11/2007 |
| EP | 1878695 | 1/2008 |
| EP | 2033973 | 3/2009 |
| EP | 2033974 | 3/2009 |
| EP | 2336195 | 6/2011 |
| EP | 2336196 | 6/2011 |
| EP | 2336222 | 6/2011 |
| GB | 13252 | 1/1909 |
| GB | 529262 | 11/1940 |
| GB | 583533 | 12/1946 |
| GB | 591858 | 9/1947 |
| GB | 600871 | 4/1948 |
| GB | 842743 | 7/1960 |
| GB | 1282926 | 7/1972 |
| JP | 55087741 | 7/1980 |
| JP | 2006206579 | 8/2006 |
| JP | 2010143861 | 7/2010 |
| JP | 2010202548 | 9/2010 |
| RU | 2119427 | 9/1998 |
| RU | 2158192 | 10/2000 |
| RU | 2176998 | 12/2001 |
| RU | 2203266 | 4/2003 |
| RU | 2319690 | 3/2008 |
| WO | WO 84/03304 | 8/1984 |
| WO | WO 87/00205 | 1/1987 |
| WO | WO 89/10362 | 11/1989 |
| WO | WO 96/40609 | 12/1996 |
| WO | WO 97/47579 | 12/1997 |
| WO | WO 98/1998 | 5/1998 |
| WO | WO 99/67409 | 12/1999 |
| WO | WO 02/04084 | 1/2002 |
| WO | WO 03/085071 | 10/2003 |
| WO | WO 2005/058856 | 6/2005 |
| WO | WO 2005/070867 | 8/2005 |
| WO | WO 2006/063220 | 6/2006 |
| WO | WO 2007/023173 | 3/2007 |
| WO | WO 2008/137639 | 11/2008 |
| WO | WO 2009/012445 | 1/2009 |
| WO | WO 2009/046537 | 4/2009 |
| WO | WO 2009/046538 | 4/2009 |
| WO | WO 2009046524 | 4/2009 |
| WO | WO 2009/130386 | 10/2009 |
| WO | WO 2009/156842 | 12/2009 |
| WO | WO 2010/009548 | 1/2010 |
| WO | WO 2010/009549 | 1/2010 |
| WO | WO 2010/009551 | 1/2010 |
| WO | WO 2010/030617 | 3/2010 |
| WO | WO 2010/083600 | 7/2010 |
| WO | WO 2010/083601 | 7/2010 |
| WO | WO 2010/104722 | 9/2010 |
| WO | WO 2010/0124381 | 11/2010 |
| WO | WO 2010/138957 | 12/2010 |
| WO | WO 2010/141950 | 12/2010 |
| WO | WO 2011/000030 | 1/2011 |
| WO | WO 2011/002660 | 1/2011 |
| WO | WO 2011/019403 | 2/2011 |
| WO | WO 2011/020082 | 2/2011 |
| WO | WO 2011/022811 | 3/2011 |
| WO | WO 2011/022812 | 3/2011 |
| WO | WO 2011/022840 | 3/2011 |
| WO | WO 2011/124639 | 10/2011 |
| WO | WO 2011/154967 | 12/2011 |
| WO | WO 2011/161141 | 12/2011 |
| WO | WO 2011/163348 | 12/2011 |
| WO | WO 2012/015616 | 2/2012 |
| WO | WO 2012/031356 | 3/2012 |
| WO | WO 2013/106137 | 7/2013 |

OTHER PUBLICATIONS

Beale, et al., "Biosynthesis of o-aminolevulinic acid from the intact carbon skeleton of glutamic acid in greening barley", Proc. Nat. Acad. Sci. USA, vol. 72, No. 7, 1975, pp. 2719-2723.

Bozell, et al., "Production of levulinic acid and use as a platform chemical for derived products", Resources, Conservation, and Recycling, No. 28, 2000, pp. 227-239.

Cha, et al., "Levulinic acid production based on extrusion and pressurized batch reaction", Industrial Crops and Products, No. 16, 2002, pp. 109-118.

Chang, et al., "Levulinic acid production from wheat straw", Biosource Technology, No. 98, 2007, pp. 1448-1453.

Chun, et al., "Kinetics of Levulinic Acid Formation from Glucose Decomposition at High Temperature", Chinese J. Chem, Eng., No. 14(5), 2006, pp. 708-712.

Chun, et al., "Kinetic Studies on Wheat Straw Hydrolysis to Levulinic Acid", Chinese J. Chem, Eng., No. 17(5), 2009, pp. 835-839.

Cox, et al., "Industrial Uses for Cane Sugar", Industrial and Engineering Chemistry, vol. 25, No. 9, 1933, pp. 967-968.

Dautzenberg, et al., "Bio Based Fuels and fuel additives from lignocellulose feedstock via the production of levulinic acid and furfural", Holzforschung, vol. 65, 2011, pp. 439-451.

Doll, et al., "Synthesis of Branched Methyl Hydroxy Stearates Including an Ester from Bio-Based Levulinic Acid", Ind. Eng. Chem. Res. No. 46, 2007, pp. 3513-3519.

Elliot, "Conversion of Biomass Wastes to Levulinic Acid and Derivatives", Success Story, Jan. 8, 1999, 1 page.

Fang, et al., "Experimental studies for levulinic acid production from whole kernel grain sorghum", Biosource Technology, No. 81, 2002, pp. 187-192.

Ganjyal, et al., "Freezing points and small scale deicing tests for salts of levulinic acid made from grain sorghum", Biosource Technology, No. 98, 2007, pp. 2814-2818.

Girisuta, Levulinic "Acid from Lignocellulosic Biomass", Nov. 5, 2007, 160 pages.

Girisuta et al., "A kinetic study on the decomposition of 5-hydroxymethylfurfural into levulinic acid", Green Chum, No. 8, 2006, pp. 701-709.

Girisuta, et al., "Experimental and kinetic modeling studies on the acid-catalysed hydrolysis of the water hyacinth plant to levulinic acid", Biosource Technology, No. 99, 2008, pp. 8367-8375.

Girisuta, et al., "Kinetic Study on the Acid-Catalyzed Hydrolysis of Cellulose to Levulinic Acid", Ind. Eng. Chem. Res. No. 46, 2007, 1696-1708.

Grote, et al. "On Levulinic Acid", reports from Annalen der Chemie, 1876, 6 pages.

Hegner, et al., "Conversion of cellulose to glucose and levulinic acid via solid-supported acid catalysis", Tetrahedron Letters, No. 51, 2010, pp. 2356-2358.

Horvat, et al., "Mechanism of levulinic acid formation" Tetrahedron Letters, No. 17, vol. 26, 1985, pp. 2111-2114.

(56) References Cited

OTHER PUBLICATIONS

International Search Report and Written Opinion from related International Application PCT/US2014/025581, dated Aug. 28, 2014, 9 pages.
Jeong, et al. "Production of Sugars and Levulinic Acid from Marine Biomass Gelidium amansii", Appl. Biochem Biotechnol, No. 161, 2010, pp. 41-52.
Jow, et al., "Dehydration of d-fructose to levulinic acid over LZY zeolite catalyst", Biomass No. 14, 1987, pp. 185-194.
Kobayashi, et al., "Analysis on residue formation during wood liquefaction with polyhydric alcohol", J. Wood Sci., No. 50, 2004, pp. 407-414.
Kuster, 5-Hyrdoxymethylfurfural (HMF), A Review Focusing on its Manufacture, Starch, No. 42(8), 1990, pp. 314-321.
Langlois, et al., Pseudo Esters of Levulinic Acid, vol. 70, 1948, pp. 2624-2626.
Leonard, "Levulinic Acid as a Basic Chemical Raw Material", Industrial and Engineering Chemistry, vol. 48, No. 8, 1956, pp. 1330-1341.
MIT OpenCourseWare, 8.4—Extraction and Washing Guide, http://ocw.mit.edu, Jan. 2012, 4 pages.
Office of Industrial Technologies, Manufacture of Industrial Chemicals from Levulinic Acid: A New Feedstock for the Chemicals Industry, 1999, 2 pages.
Office of Industrial Technologies, Commercialization of the Biofine Technology for Levulinic Acid Production From Paper Sludge, 1998, 2 pages.
Olson, "Final Report—Subtask 4.1—Conversion of Lignocellulosic Material to Chemicals and Fuels", Jun. 2001, 16 pages.
Park, et al., "Enzymatic Synthesis of Rubber From Mevalonic Acid", Mar. 18, 1958, 4 pages.
Peng, et al., "Catalytic Conversion of Cellulose to Levulinic Acid by Metal Chlorides", Molecules No. 15, 2010, pp. 5258-5272.
Rackermann, et al., "The conversion of lignocellulosics to levulinic acid", Biofuels, Bioproducts and Biorefining, No. 5(2), 2011, pp. 115-126.
Salak, et al., "Kinetics of the Decomposition of Fructose Catalyzed by Hydrochloric Acid in Subcritical Water: Formation of 5-Hydroxymethylfurfural, Levulinic, and Formic Acids", Ind. Eng. Chem. Res. No. 46, 2007, pp. 7703-7710.
Schuette, et al., "Normal Valerolactone. III. Its Preparation by the Catalytic Reduction of Levulinic Acid With Hydrogen in the Presence of Platinum Oxide", Preparation of n-Valerolactone, vol. 52, Jul. 1930, pp. 3010-3012.
Shaw, et al., "Acid catalyzed degradation of d-fructose", Carbohydrate Research, No. 5, 1967, pp. 266-273.
Sriram, et al., "Identification of hexose hydrolysis products in metabolic flux analytes: A case study of levulinic acid in plant protein hydrolysate", Metabolic Engineering, No. 9, 2007, pp. 442-451.
Qi, et al., "Sulfated Zirconia ss a Solid Acid Catalyst for the Dehydration of Fructose to 5-Hydroxymethylfurfural", Catalysis Communications, No. 10, 2009, pp. 1771-1775.
Taherzadeh, et al., "Characterization and Fermentation of Dilute-Acid Hydrolyzates From Wood", Ind. Eng. Chem. Res., No. 36, 1997, pp. 4659-4665.
Thomas, et al., "Studies on Levulinic Acid. I. Its Preparation From Carbohydrates by Digestion with Hydrochloric Acid Under Pressure", Preparation of Levulinic Acid, vol. 53, 1931, pp. 2324-2328.
Uslu, et al., "Reactive Extraction of Levulinic Acid by Amberlite LA-2 Extractant", J. Chem. Eng. Data, No. 54, 2009, pp. 712-718.
Uslu, et al., "Equilibrium Studies of Extraction of Levulinic Acid by (Trioctylamine (TOA) = Ester) Solvents", J. Chem. Eng. Data, No. 53, 2008, pp. 1557-1563.
Van Dam, et al ."The Conversion of Fructose and Glucose in Acidic Media—Formation of Hydroxymethylfurfural", Starch 38, Nr. 3, S, 1986, pp. 95-101.
Watts, "A Dictionary of Chemistry and the Allied Branches of Other Sciences", 1881, pp. 1181-1182.
Weiss, et al., "The Enzymatic Synthesis of Triglycerides", Communications to the Editor, vol. 78, 1956, p. 3550.
Yamada, et al., "Characterization of the products resulting from ethylene glycol liquefaction of cellulose", J. Wood Sci., No. 47, 2001, pp. 458-464.
Yanada, et al., "Rapid liquefaction of lignocellulosic waste by using ethylene carbonate", Biosource Technology, No. 70, 1999, pp. 61-67.
Zhao, et al., "Metal Chlorides in Ionic Liquid Solvents Convert Sugars to 5-Hydroxymethylfurfural" Science, vol. 316, Jun. 15, 2007, pp. 1597-1600.
Zhao, et al., "Effects of Crystallinity on Dilute Acid Hydrolysis of Cellulose by Cellulose Ball-Mining Study", Energy & Fuels, No. 20, 2006, pp. 807-811.

\* cited by examiner

PROCESS TO PREPARE LEVULINIC ACID

CROSS REFERENCE TO RELATED APPLICATIONS

This application is a continuation of U.S. Ser. No. 13/831,317, filed Mar. 14, 2013, which claims priority to U.S. Provisional Patent Application No. 61/722,766, filed Nov. 5, 2012, all entitled "PROCESS TO PREPARE LEVULINIC ACID", the contents of which are incorporated herein in their entirety for all purposes.

FIELD OF THE INVENTION

The invention relates generally to the preparation and purification of levulinic acid.

BACKGROUND OF THE INVENTION

Levulinic acid can be used to make resins, plasticizers, specialty chemicals, herbicides and used as a flavor substance. Levulinic acid derivatives are useful as solvents, and as a starting materials in the preparation of a variety of industrial and pharmaceutical compounds such as diphenolic acid (useful as a component of protective and decorative finishes), calcium levulinate (a form of calcium for intravenous injection used for calcium replenishment and for treating hypocalcemia. The use of the sodium salt of levulinic acid as a replacement for ethylene glycols as an antifreeze has also been proposed.

Esters of levulinic acid are known to be useful as plasticizers and solvents, and have been suggested as fuel additives. Acid catalyzed dehydration of levulinic acid yields alpha-angelica lactone.

Levulinic acid has been synthesized by a variety of chemical methods. But levulinic acid has not attained much commercial significance due in part to the low yields of levulinic acid obtained from most synthetic methods. Yet, another reason is the formation of a formic acid byproduct during synthesis and its separation from the levulinic acid. Therefore, the production of levulinic acid has had high associated equipment costs. Despite the inherent problems in the production of levulinic acid, however, the reactive nature of levulinic acid makes it an ideal intermediate leading to the production of numerous useful derivatives.

Cellulose-based biomass, which is an inexpensive feedstock, can be used as a raw material for making levulinic acid. The supply of sugars from cellulose-containing plant biomass is immense and replenishable. Most plants contain cellulose in their cell walls. For example, cotton comprises 90% cellulose. Furthermore, it has been estimated that roughly 75% of the approximate 24 million tons of biomass generated on cultivated lands and grasslands are waste. The cellulose derived from plant biomass can be a suitable source of sugars to be used in the process of obtaining levulinic acid. Thus, the conversion of such waste material into a useful chemical, such as levulinic acid, is desirable.

BRIEF SUMMARY OF THE INVENTION

There are a few major issues in producing levulinic acid form biomass. First, levulinic acid is difficult to separate from the mineral acid catalysts (sulfuric acid or HCl) or the byproducts, especially from formic acid and char. Secondly, current processes generally require high temperature reaction conditions, generally long digestion periods of biomass, specialized equipment to withstand hydrolysis conditions, and as a result, the yield of the levulinic acid is quite low, generally in yields of less than 50 stoichiometric percent or less. Also, the solids obtained under the current reaction conditions can result in fouling of the reactor and downstream equipment due to plugging or sticking of the char to the internals of the equipment.

Therefore, a need exists for a new approach that overcomes one or more of the current disadvantages noted above.

The present invention surprisingly provides novel approaches to more efficiently prepare levulinic acid in commercial quantities with high yields and high purities. Additionally, the production of 5-hydroxymethyl-2-furaldehyde (HMF) intermediate is also described, which is an important intermediate to the product of levulinic acid.

In one aspect, the use of high concentration of acid, e.g., about 20-80 weight percent based on the total weight of reaction components and low reaction temperature (approximately 60-160° C.) helps to improve yield of desired products with reduction of undesired byproducts. This is one attribute, but there are more.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention provides various advantages in the preparation of levulinic acid, hydroxymethyl furfural and/or formic acid. The following list of advantages is not meant to be limiting but highlights some of the discoveries contained herein.

First, a biomass material can be used as the initial feedstock to prepare the levulinic acid, hydroxymethyl furfural and/or formic acid. This ability provides great flexibility in obtaining a constant source of starting material and is not limiting.

Second, the biomass can be a refined material, such as fructose, glucose, sucrose, mixtures of those materials and the like. As such, there is a plentiful supply of materials that can be converted into the ultimate product(s). For example, sugar beets or sugar cane can be used as one source. Fructose-corn syrup or glucose syrup are other readily available materials. Use of such materials thus helps to reduce the costs to prepare the desired products.

Third, it has been discovered that use of high concentrations of acid(s), generally about 20 weight percent or more (based on the total mass of the reaction medium) provides a cleaner reaction product with less char and unwanted byproducts. It has also been found that use of high concentrations of acid(s), generally up to 80 weight percent or more, (based on the total mass of the reaction medium) provides faster reaction times than lower acid concentrations used with the same reaction conditions.

Fourth, it has also been discovered that with the use of higher concentrations of acid, the reaction conditions can be conducted at much lower temperatures than are currently utilized in the literature. Again, this lessens the amount of char and byproducts from the reaction(s) that take place and increases the yield of the desired product(s).

Fifth, it has also been discovered that with the methods of the present invention, the char that is created is much easier to remove from the reactor and the char remains well-dispersed in the reaction medium.

Sixth, it has also been found that the advantages of the new process conditions, including continuous addition of the biomass over a period of time during the reaction can be incorporated into existing processes to improve yield, reduce costs, improve efficiency and improve purity of product(s).

Seventh, the processes described herein can be performed via CSTR or continuous batch process conditions.

Eighth, an integrated process with recycling and removal of impurities is also provided herein.

Ninth, use of highly selective extraction solvents which extract LA, but minimal amounts of sulfuric acid from the reaction medium are provided herein.

In one embodiment, This process uses a high concentration of sulfuric acid, which has several distinct advantages. For one, the reactions can be run at lower temperatures compared to low acid processes and still hydrolyze the sugars in a reasonable time frame. It has been discovered that under these high acid, low-temperature reaction conditions (e.g., 60-160° C., preferably, 80-150° C., and more preferably, 90-140° C.), the char byproduct that is formed is in the form of suspended particles that are easier to remove from the reactor and that can be filtered from the liquid hydrolysate product stream. In contrast, with low acid conditions, high temperature is required to effectively hydrolyze the sugar in a reasonable time frame and those conditions produce a char byproduct that coats the reactor components in such a manner that it is difficult to remove without mechanical or hydraulic energy, and for the most part does not stay suspended in the reaction mixture. This high-acid reaction strategy, however, makes it difficult to isolate the organic acid products (levulinic acid and formic acid) from the mineral acid reagent. When small amounts of sulfuric acid are used, as is typical in the prior art, the strong inorganic acid can effectively be neutralized to its salt form by careful addition of stoichiometric amounts of base. At the high acid contents used here, however, the quantity of salt produced would be excessive. Likewise, the use of an ion exchange column is impractical because the large quantity of inorganic acid would quickly fill the capacity of the column.

Solvent extraction techniques, where the organic acids are preferably extracted into an organic solvent, are preferred. Even here, the high mineral acid content poses challenges. The organic solvent should be insoluble in the aqueous phase, but in some cases, the sulfuric acid can drive compatibility of the organic solvent and the aqueous phase. When this happens, a portion of the organic solvent becomes soluble in the concentrated sulfuric acid aqueous phase and the risk of solvent loss to side reactions increases. Even if the organic solvent is stable in the aqueous sulfuric acid phase, the organic solvent must be recovered from the aqueous stream before recycling the raffinate back to the reaction unit in order to maintain optimum reaction selectivity to form LA or inoperability due to solids agglomeration in the reactor due to side reactions with the extraction solvent. High mineral acid concentration also carries with it the potential for higher mineral acid concentrations in the organic extract phase. When this happens, there is the risk of solvent loss and LA loss to side reactions catalyzed by the mineral acid, particularly in the case when the organic stream is heated to distill the organic solvent. Therefore, solvent extraction of the organic acid products should ideally have at least some of the following characteristics:

little to no miscibility with water;

little to no miscibility with the mineral acid;

selectively partition the organic acids into the organic solvent phase;

have low partitioning of the mineral acid into the organic solvent phase;

have low reactivity between the organic extraction solvent and the mineral acid;

have low reactivity between the organic extraction solvent & the organic acid products;

have the ability to remove or reduce any mineral acid that partitions into the organic phase;

easy to remove from organic acid, such as by backwashing or distillation;

allow the neutralization or water-washing of the mineral acid.

In one embodiment, the partition coefficient of the extraction solvent for levulinic acid is at least 0.3, more specifically, at least 0.5, more specifically, at least 0.7, more specifically, at least 1.0, more specifically at least 1.3, more specifically, at least 1.5 more specifically, at least 1.7, and more specifically at least 2.0, 3 and 4. In one embodiment, the partition coefficient of the extraction solvent for formic acid is at least 0.3, more specifically, at least 0.5, more specifically, at least 0.7, more specifically, at least 1.0, more specifically at least 1.3, more specifically, at least 1.5 more specifically, at least 1.7, and more specifically at least 2.0, more specifically, at least 2.3, more specifically, at least 2.5, more specifically, at least 3.0, more specifically, at least 3.5, more specifically, at least 4.0, more specifically, at least 5.0 more specifically, at least 6.0, more specifically, at least 7.0, more specifically, at least 8.0, and more specifically, at least 9.0.

In one aspect, the invention is directed to a process to make crystallizable levulinic acid ("LA") from sugar solutions.

Hydrolysis of an aqueous solution of sucrose, glucose, fructose, or blends of the aforementioned, specifically fructose and sucrose, occurs in a batch or continuous reactor, specifically a continuously fed batch-reactor. In one embodiment the method includes the following steps following hydrolysis of a solution of sucrose, glucose, fructose, or blends of the aforementioned:
  (a) Filtration of solids from hydrolysate mixture.
  (b) Water or extraction solvent wash of solids (optional).
  (c) Extraction of LA and formic acid from aqueous hydrolysate into an extraction solvent.
  (d) Removal of extraction solvent by distillation.
  (e) Optional Thin-film evaporation of LA.
  (f) Optional Crystallization of LA
  (g) Recycling of extraction solvent to liquid extraction step.
  (h) Recycling of raffiante phase back to reactor.
  (i) recovery of formic acid.

The process allows fast reaction time, easy to handle char byproduct, good yields, no neutralization step (optional), efficient extraction and distillation to afford a crystallizable LA product.

A few processes are known to make LA from sugar, but little is known on how to remove the LA and formic acid from the reactor and purify it from the hydrolysate. The disclosed process produces approximately >80% purity LA that may be distilled or crystallized to a purity >95%.

Unless otherwise noted, the concentration of sulfuric acid used is 96-98%.

Integrated Process Description

An integrated process to synthesize and isolate levulinic acid (LA) using recycled mineral acid is described herein. The integrated process includes:

a) providing an aqueous solution of >1% LA in an aqueous mixture comprising 20-80% by weight mineral acid and >0.1% suspended solids from the method comprising the steps:
  b) heating an aqueous solution of a mineral acid to a temperature from about 60° C. to about 160° C. in a reactor, wherein the mineral acid is present from at least 20 percent by weight to about 80 percent by weight; and
  c) adding a monosaccharide or di-saccharide to the heated aqueous acid in the reactor to form a reaction mixture at a rate such that the monosaccharide content of the reaction mixture remains less than or equal to about 5% by weight of the reaction mixture, to provide levulinic acid; and
  d) removing the suspended solids by filtration to make a filtrate with <0.099% suspended solids,
  e) optionally, washing the solids with water or an aqueous base solution and optionally combining the wash with the filtrate
  f) extracting the LA from the filtrate of step b (and optionally, c) using an extraction solvent comprising, preferably, a phenolic or substituted phenolic compounds to provide an extract phase containing levulinic and formic acid and a raffinate phase; and
  g) removing the strong acid impurities from the extract phase to a level below 1%, prior to formic acid separation or extract solvent distillation; and
  h) removing formic acid by evaporation or distillation from the solvent and levulinic acid; and
  i) removing the solvent from levulinic acid and recycling it back into an extraction unit; and
  j) evaporating or distilling any excess water and formic acid form the raffinate phase;
  k) removing any extraction solvent, preferably, a phenolic or substituted phenolic solvent impurities from the raffinate phase to a level below 1%; and
  l) recycling the raffinate back to the reactor in order to recycle the acid catalyst in the raffinate.

Preferable LA concentrations in the aqueous solution of step a) are >1%, >2%, >4%, >5%, preferably between 5-10%.

Preferable strong acid concentration in the solvent phase in step g) is <0.8%, <0.5%, <0.2%, and more preferably <0.1%.

Preferably the extraction solvent is a phenolic or substituted phenolic solvent comprises cresol isomers, 2,4-xylenol, or mixtures of xylenol isomers.

Step g) may be accomplished by extraction with water, neutralization with a weak base anion exchange resin, or neutralization with an inorganic base; <0.1%, <0.05%, or <0.01% levels of strong acid are preferred.

Preferably the amount of water used in step g) is <20% by weight of the extract.

Preferably the inorganic base in step g) is an aqueous solution of $NaOH$, $NaHCO_3$, $Na_2CO_3$, $Ca(OH)_2$, $CaCO_3$, $Na_3PO_4$, $K_3PO_4$, $Ca_3(PO_4)_2$, $BaCO_3$, $Ba(OH)_2$, $NH_3$, $NH_4OH$ or mixtures thereof.

Step k) may be accomplished by adsorption with activated carbon or by extraction with a hydrocarbon solvent; Preferably the solvent used in step i) is a C5-C24 straight chain, cyclic, or branched hydrocarbon, an aromatic hydrocarbon, or mineral oil.

Preferably the level of phenolic or substituted phenolic solvent in the raffinate is <0.1%, <0.05%, or <0.02% prior to step 1).

The process steps (a-l) may be continuous, batch, or semi-continuous. The process may comprise holding tanks in between steps. The process may also contain purge streams for the recycled raffinate stream and the recycled solvent stream.

Continuous-Fed Batch Description

A batch reactor comprises an initial mixture of sulfuric acid and water, wherein the sulfuric acid concentration is 20-80 wt % of the mixture. The mixture is heated to a temperature of 60-160° C. The contents are stirred with an agitator and optionally recirculated in the reactor. An aqueous solution comprising mono-saccharides and/or di-saccharides is continuously added into the reactor such that the concentration of monosaccharides or the intermediate, 5-hydroxymethyl-2-furaldehyde (HMF) does not exceed 5% by weight of the total mixture at any moment in time. Alternatively, the aqueous solution of monosaccharides and disaccharides is continuously added into the reactor such that the feed rate is between 0.15-80 lbs/hour per 100 pounds of the initial mixture of sulfuric acid and water. After the addition of mono-saccharides and di-saccharides, the reaction mixture is optionally held for 5-180 minutes between 60-160° C. Alternatively, after the addition of monosaccharides and disaccharides into the reactor, the reaction mixture is heated to 120-160° C. and held for 5-180 minutes. The reaction mixture is emptied from the reactor when the total amount of monosaccharides is <2%, preferably <1%, more preferably <0.1% and when the total amount of HMF is <1%, preferably <0.1%, more preferably <0.05%

Other embodiments: the sugar feeds may be heated from 40-110° C. prior to addition into the reactor.

After the reaction, the contents may be cooled when flowing out of the reactor or the reaction mixture may be cooled in the reactor prior to emptying the reaction mixture out of the reactor.

The char or solids remains suspended in the reaction mixture throughout the entire reaction.

Examples of continuous addition batch reactions are shown in Examples 1 through 8 in the following examples section.

Biomass

Biomass, as used herein, includes sludges from paper manufacturing process; agricultural residues; bagasse pity; bagasse; molasses; aqueous oak wood extracts; rice hull; oats residues; wood sugar slops; fir sawdust; corncob furfural residue; cotton balls; raw wood flour; rice; straw; soybean skin; soybean oil residue; corn husks; cotton stems; cottonseed hulls; starch; potatoes; sweet potatoes; lactose; sunflower seed husks; sugar; corn syrup; hemp; waste paper; wastepaper fibers; sawdust; wood; residue from agriculture or forestry; organic components of municipal and industrial wastes; waste plant materials from hard wood or beech bark; fiberboard industry waste water; post-fermentation liquor; furfural still residues; and combinations thereof, sugar, a C6 sugar, a lignocelluloses, cellulose, starch, a polysaccharide, a disaccharide, a monosaccharide or mixtures thereof.

Reactors

One, optionally two, reactors are used to convert fructose to the desired products. The reactors are optionally vented to maintain an internal pressure; the vent stream is optionally collected to recover steam and formic acid product; the vent stream can all be returned to the reactor as a reflux. If there are two reactors in series, the first reactor is optionally controlled at a different temperature and at a high concentration of acid in order to achieve desired conversion and selectivity. The first reactor would generally be controlled at a lower temperature than the second. Optionally, a process step between the two reactors may be used to separate "tar" solids and/or to preferentially extract the reaction products (away from the aqueous feed) to feed into the second reactor.

The reactors may be operated in a batch-wise (wherein the reactants are continuously or pulsed-fed to the reactor and the reaction continues until the desired degree of conversion, and the products are then emptied from the reactor) or in a continuous fashion (wherein reactants are fed continuously and the products are removed continuously). In one embodiment, the reactors are run in a continuously-fed batch fashion. In another embodiment, the reactors are run in a continuous mode.

The agitation in the reactors should be adequate to prevent agglomeration of solid co-products which may be formed during the reaction. Specifically, the reactors should be designed with sufficient axial flow (from the center of the reactor to the outer diameter and back).

Flash (Optional)

The reaction products may be optionally cooled in a "flash" process. The flash step rapidly cools the reaction products by maintaining a pressure low enough to evaporate a significant fraction of the products. This pressure may be at or below atmospheric pressure. The evaporated product stream may be refluxed through stages of a distillation column to minimize the loss of desired reaction products, specifically levulinic acid, and to ensure recovery of formic acid reaction.

The "bottoms" or less volatile stream from the flash step is advanced to the solids separation stage.

Solids Separation

In the solids separation stage of the process, the solvent and desired reaction products, specifically levulinic acid and formic acid, are separated from any solids which may have formed during the reaction phase. The solids may be separated through a combination of centrifuge, filtration, and settling steps (ref Perrys Chemical Engineering Handbook, Solids Separation). The separated solids may be optionally washed with water and solvents to recover desired reaction products or solvent which may be entrained in or adsorbed to the solids. It has been found that in some embodiments, such as those reactions employing high levels of mineral acid (greater than 20%) that are reacted at lower temperatures, such as between 60-160° C., the solids may have density properties similar to the liquid hydrolysate which effectively allows the solids to be suspended in solution. In these embodiments, certain separation techniques such as centrifugation are not as effective. In these embodiments filtration utilizing filter media having a pore size less than about 20 microns has been found to effectively remove solids from the mixture. When removing solids from the system a solid "cake" is formed. It is desirable that the cake be up to 50% solids. Thus any separation technique that obtains a cake having a higher amount of solids is preferred. A certain amount of LA and mineral acid will be present in the cake and it may be desirable to wash the cake with an extraction solvent or water to recover LA.

It has also been surprisingly found that the solid particles in the high mineral acid and lower temperature embodiments are easily filtered and do not inhibit flow as the cake is formed. It is believed that the properties of the char formed under these process conditions are such that any cake remains porous enough that a small filter size (less than 20 microns) can be utilized while maintaining a high flow rate through the medium.

The isolated solids may be incinerated to generate power or disposed.

The liquid stream, comprising (but not limited to) water, acid, solvent, levulinic acid, formic acid, and some "soluble tars" are advanced to the extraction stage of the process.

Extraction

In the extraction stage of the process, the liquid stream is mixed with an extraction solvent stream. The preferred extraction solvent dissolves levulinic acid more effectively than the other products in the liquid stream. The preferred solvent does not dissolve significantly into the water phase. Extraction configurations are preferably multi-stage and continuous, as described in Perry's Chemical Engineering Handbook. The extraction system may be in a vertical column, preferably in which the fluids are contacted in a counter current fashion. The extraction system may be a KARR® (KMPS, Inc.) or SCHEIBEL® column (KMPS, Inc.), a packed column, or a tray-type column. The column may have multiple stages. The extraction system may also be a fractional extraction system. A water-wash may also be conducted on the solvent phase after the extraction solvent has contacted the aqueous reactor composition in the extraction system. The extractions system may be conducted at temperatures from 20-90° C. The extraction system may contain mixing stages.

Alternatively, the extraction system may contain one or more mixer-settlers in series that allow extraction of LA form the aqueous reactor composition into the extraction solvent. The mixer-settler system may have multiple stages. A water-wash may also be conducted on the solvent phase after the extraction solvent has contacted the aqueous reactor composition in the mixer-settler extraction system. The mixer-settler extraction system may be conducted at temperatures from 20-90° C. The mixer-settler extraction system may contain one or more mixing stages and one or more settling stages.

Suitable extraction solvents include, for example but are not limited to, phenol, 4-methoxyphenol, 2-methoxyphenol, 3-methoxyphenol, 2-sec-butyl phenol, 3-sec-butyl phenol, 4-sec-butyl phenol, 2-t-butyl phenol, 4-t-butyl phenol, 2,4-di-t-butyl phenol, 2,4-di-methoxyphenol, 2-methylphenol, 3-methylphenol, 4-methylphenol, 2,3-xylenol, 2,4-xylenol, 2,5-xylenol, 2,6-xylenol, 3,4-xylenol, or 3,5-xylenol, 4-hexyl-resorcinol, butylated hydroxyl-toluene (BHT), 2,5-dimethoxyphenol, 3,5-dimethoxy phenol, 2,6-dimethoxy phenol, nonylphenol, or mixtures thereof.

Additional suitable extraction solvent include, for example but are not limited to, methyl isoamyl ketone, methyl isobutyl ketone, diisobutyl ketone, acetophenone, cyclohexanone, isophorone, neopentyl alcohol, isoamyl alcohol, n-hexanol, n-heptanol, 2-ethyl hexanol, n-octanol, 1-nonanol, 1-undecanol, phenol, 4-methoxyphenol, guaiacol, methylene chloride, methyl isobutyl carbinol, anisole, ethylene glycol di-n-butyl ether, castor oil, 1H, 1H, 2H, 2H-pentadecafluorooctanoic acid, 1H, 1H, 2H, 2H-pentadecafluorooctanol, 2-ethyl-hexanoic acid, propyl-substituted bisphenols with PDMS linking groups, diethyl carbonate, halogen-substituted phenols or bisphenols, and mixtures thereof.

The aqueous raffinate is recycled to the reactor phase, after optional distillation or purification steps to adjust the relative concentrations of solvent, water, and acid in the raffinate.

The extract solvent phase contains levulinic acid and formic acid and is progressed to the solvent removal stage of the process.

Suitable solvents to extract LA include, for example, polar water-insoluble solvents such as p-methoxy-phenol and 2,4-xylenol/2,5-xylenol mixtures. Such solvents are used generally at room temperature so as not to serve as potential reaction component.

Solvent Removal

Levulinic acid may be separated from the solvent phase by evaporating or distilling the solvent. Alternatively, the levulinic acid may be crystallized from the solvent phase in a crystallization process. The solvent removal process may be a combination of distillation and crystallization. The recovered solvent may be recycled to the extraction step.

The resulting stream of highly concentrated levulinic acid may be advanced for further chemical derivatization or may be further purified in another distillation step such as high vacuum wipe-film-evaporation, crystallization or falling film evaporation. Preferably the levulinic acid stream is kept at a low temperature throughout the solvent removal steps to inhibit the formation of angelica lactone.

Mineral Acids

Suitable acids used to convert the biomass materials described herein, including sugars, include mineral acids, such as but not limited, to sulfuric acid, hydrochloric acid, hydrobromic acid, hydroiodic acid, hydrofluoric acid, perchloric acid and mixtures thereof.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Analytical Methods:
HPLC Methods
1. Waters LC 2695 with PDA 2998
Column Hamilton×300 7 μm 250×4.1 mm
Flow: Isocratic 2.0 mL/min
Sample Temp Target 25.0° C., Column Temp Target 50.0° C.
Mobile Phase: 20% Methanol 80% 20 mN Phosphoric acid 2. Waters LC 2695 with PDA 2998
Column: Hamilton×300 7 μm 250×4.1 mm
Flow: Gradient 2.0 mL/min
Sample Temp Target 25.0° C., Column Temp Target 50.0° C.
Mobile Phase: Solvent B=Methanol, Solvent D=20 mN Phosphoric acid in deionized water

| Gradient Table | | | | |
| --- | --- | --- | --- | --- |
| | Time | Flow | % B | % D |
| 1 | | 2.00 | 0.00 | 100.0 |
| 2 | 0.50 | 2.00 | 0.00 | 100.0 |
| 3 | 0.51 | 2.00 | 12.0 | 88.0 |
| 4 | 5.00 | 2.00 | 12.0 | 88.0 |
| 5 | 10.00 | 2.00 | 40.0 | 60.0 |
| 6 | 13.00 | 2.00 | 40.0 | 60.0 |
| 7 | 13.01 | 2.00 | 0.0 | 100.0 |
| 8 | 15.00 | 2.00 | 0.0 | 100.0 |

3. Waters LC 2695 with RI 2414
Column: Bio-Rad Aminex HPX-87H, 300×7.8 mm
Flow: Isocratic 0.60 mL/min
Sample Temp Target 25.0° C., Column Temp Target 50.0° C.
Mobile Phase: 20 mM Phosphoric acid in deionized water with 3% Acetonitrile 4. Waters LC 2695 with RI 2414
Column: Supelcosil LC-$N_2$
Flow: Isocratic 1.0 mL/min
Sample Temp Target 25.0° C., Column Temp Target 50.0° C.
Mobile Phase: 80% Acetonitrile 20% Water 20 mM Phosphoric acid Char Washing Method (Unless Otherwise Specified)

The char was placed in a Buchner funnel and first washed with 2×250 mL deionized water and a spatula was used to break up the char cake so that it was fully dispersed in the water on the Buchner funnel. After the water wash the char was washed with 250 mL of acetone.

Moisture Analyzer

Mettler Toledo HG63 Halogen Moisture Analyzer Drying Temperature: 125° C.

Example 1

2.5 hr Con-Add

Into a beaker containing a magnetic stir bar charged 43.25 g (0.24 mol) fructose and 50.08 g deionized water. The beaker was placed on a stir plate to dissolve the fructose. Into a 500 mL four neck round bottom flask containing a magnetic stir bar charged 11.84 g deionized water and 153.35 g (1.00 mol) 64% sulfuric acid. The round bottom flask was situated in a heating mantle and equipped with a thermocouple, condenser, glass stopper and syringe pump tube. The sulfuric acid and water mixture was heated to 90° C. while stirring at a rate of 650 RPM. Once the fructose was all dissolved it was charged into two 60 mL syringes and situated into a syringe pump. Once the acid and water mixture was up to temperature the fructose solution started to be added via the syringe pump. The fructose solution was added over a course of 2.5 hours at a rate of 30.8 mL/hr. The concentration of fructose did not exceed 0.7%, and the concentration of HMF did not exceed 0.4% during the monosaccharide addition into the reactor. After all of the fructose had been added, the reaction was left to react for an additional hour and then was shut down and allowed to cool to ambient temperature. The solids that were formed remained suspended in the reactor during the entire reaction. Once the reaction mixture was cool it was filtered through a glass microfiber 1.1 μm filter paper. The solids were then washed with DI water and acetone. The moisture analyzer was used to determine the amount of solids in the reaction mixture. The results of the experiment showed 57.91 mol % yield of LA, 68.01 mol % yield of FA and an LA to char ratio of 2.18 using HPLC method 3.

Example 2

2.5 hr Con-Add

The same procedure was followed as in Example 1 with different charged weights and two different feed rates were used to add in the fructose solution. 43.28 g (0.24 mol) fructose and 25.03 g deionized water. 36.86 g deionized water and 153.41 g (1.00 mol) 64% sulfuric acid. For the first 75 minutes of the reaction the syringe pump rate was set to 25.48 ml/hr then for the remaining 75 minutes the syringe pump rate was set to 13.72 mL/hr. The concentration of fructose did not exceed 1%, and the concentration of HMF did not exceed 0.5% during the monosaccharide addition into the reactor. The solids that were formed remained suspended in the reactor during the entire reaction. The results of the experiment showed 59.11 mol % yield of LA, 67.47 mol % yield of FA and an LA to char ratio of 2.42 using HPLC method 3.

Example 3

0.5 hr Con-Add

The same procedure was followed as in Example 1 with different charged weights and all of the fructose was added over 30 minutes. 36.12 g (0.20 mol) fructose and 30.05 g deionized water. 97.29 g deionized water and 88.27 g (0.90 mol) sulfuric acid. The syringe pump was set to a rate of 106 mL/hr. The concentration of fructose did not exceed 3.5%, and the concentration of HMF did not exceed 1.5% during the monosaccharide addition into the reactor. The solids that were formed remained suspended in the reactor during the entire reaction. The results of the experiment showed 69.08 mol % yield of LA, 70.72 mol % yield of FA and an LA to char ratio of 2.75 using HPLC method 2 and 4.

Example 4

0.5 hr Con-Add

The same procedure was followed as in Example 1 with different charged weights. 37.90 g (0.21 mol) fructose and 26.03 g deionized water. 102.08 g deionized water and 102.99 g (1.05 mol) sulfuric acid. The syringe pump was set to a rate of 94 mL/hr. The concentration of fructose did not exceed 2.5%, and the concentration of HMF did not exceed 1% during the monosaccharide addition into the reactor. The solids that were formed remained suspended in the reactor during the entire reaction. The results of the experiment showed 82.28 mol % yield of LA, 92.14 mol % yield of FA and an LA to char ratio of 3.03 using HPLC method 1 and 4.

Comparative Example 5

0.17 hr Con-Add

The same procedure was followed as in Example 1 with different charged weights and all of the fructose was added over 10 minutes. 37.92 g (0.21 mol) fructose and 26.06 g deionized water. 102.07 g deionized water and 103.18 g (1.05 mol) sulfuric acid. The syringe pump was set to 287.4 mL/hr. The concentration of fructose did exceeded 5%, and the concentration of HMF exceeded 1% during the monosaccharide addition into the reactor. The solids that were formed remained suspended in the reactor during the entire reaction. However, the LA yield was below 60 mol % yield. The results of the experiment showed 50.59 mol % yield of LA, 69.15 mol % yield of FA and an LA to char ratio of 2.17 using HPLC method 1 and 4.

Example 6

1.25 hr Con-Add

The same procedure was followed as in Example 1 with different charged weights and all of the fructose was added over 1.25 hours. 38.03 g (0.21 mol) fructose and 25.60 g deionized water. 102.57 g deionized water and 103.04 g (1.05 mol) sulfuric acid. The syringe pump was set to 37.6 mL/hr. The concentration of fructose did not exceed 1.5%, and the concentration of HMF did not exceed 0.7% during the monosaccharide addition into the reactor. The solids that were formed remained suspended in the reactor during the entire reaction. The results of the experiment showed 81.37 mol % yield of LA, 95.03 mol % yield of FA and an LA to char ratio of 3.48 using HPLC method 1 and 4.

Example 7

2.5 hr Con-Add

The same procedure was followed as in Example 1 with different charged weights. 37.89 g (0.21 mol) fructose and 25.06 g deionized water. 103.09 g deionized water and 103.03 g (1.05 mol) sulfuric acid. The syringe pump was set to 18.8 mL/hr. The concentration of fructose did not exceed 0.6%, and the concentration of HMF did not exceed 0.5% during the monosaccharide addition into the reactor. The solids that were formed remained suspended in the reactor during the entire reaction. The results of the experiment showed 92.89 mol % yield of LA, 103.37 mol % yield of FA and an LA to char ratio of 3.75 using HPLC method 1 and 4.

Example 8

6 hr Con-Add

The same procedure was followed as in Example 1 with different charged weights and all of the fructose was added over 6 hours. 37.87 g (0.21 mol) fructose and 23.05 g deionized water. 105.13 g deionized water and 103.00 g (1.05 mol) sulfuric acid. The syringe pump was set to 6.5 mL/hr. The concentration of HMF did not exceed 0.5% during the monosaccharide addition into the reactor. The solids that were formed remained suspended in the reactor during the entire reaction. Once the reaction mixture was cool it was filtered through a fitted glass funnel and the solids were washed with 2×20 mL deionized water and then 2×20 mL methylene chloride. The solids were left to air dry overnight and the next day were placed into a vacuum oven to dry until a constant weight was achieved. The results of the experiment showed 78.69 mol % yield of LA, 91.89 mol % yield of FA and an LA to char ratio of 2.84 using HPLC method 1 and 4.

In another set of examples:
Reagents
Formic acid
Supplier: Alfa Aesar
Purity: 97%
Sulfuric acid
Supplier: Sigma-Aldrich
Purity: 95-98%
Levulinic acid
Supplier: Sigma Aldrich
Purity=98%
LBX-98
Supplier: Merisol
Mixture of 66.9% 2,4 xylenol and 30.6% 2,5 xylenol
LBX-98 mixture (Composition A)
11.24% levulinic acid
1.15% formic acid
0.41% sulfuric acid
87.2% LBX-98

Example 9

A 20 mL centrifuge tube was charged with 9.0 g of Composition A and 1.0 g of DI Water. The centrifuge tube was shaken for 30 seconds to mix the two layers. The sample rested at room temperature (17-23° C.) for 30 minutes to allow the layers to separate. The sample was then placed inside a 45° C. oven for 5 minutes to allow the layers to separate.

Sample rested, at room temperature, overnight to allow separation to continue. Separation layer was marked and sample was shaken. Sample rested at room temperature for 15 minutes to allow layers to separate. Sample then placed in a sandbath inside a 60° C. oven for 15 minutes. After checking for layer separation, samples were placed back into the oven for an additional 15 minutes. Sample rested in oven overnight and layers were separated via pipette while still warm.

Example 10

Same as example 9 but with 8.5 g of Composition A and 1.5 g DI Water.

Example 11

Same as example 9 but with 8.0 g Composition A and 2.0 g DI Water.

Example 12

Two 20 mL centrifuge tubes were charged with 8.0 g of Composition A and 2.0 g of DI Water. Before mixing, samples were heated to 50° C. in an oven. The centrifuge tubes were removed and shaken for 30 seconds to mix the layers. Samples were placed back into the oven and monitored for layer separation.

Example 13

(a) Reagents combined in example 12 were used for example 13(a) in addition to a 20 mL centrifuge tube that was charged with 8.0 g of Composition A and 2.0 g of DI Water. Before mixing, samples were heated to 60° C. in an oven. The centrifuge tubes were removed and shaken for 30 seconds to mix the layers. Samples were placed back into the oven and monitored for layer separation.

(b) Reagents combined in example 13(a) were used for example 5(b) at 70° C.

(c) Reagents combined in example 13(b) were used for example 5(c) at 80° C.

(d) Reagents combined in example 13(c) were used for example 5(d) at 90° C.

Example 14

A 20 mL centrifuge tube was charged with 8.0 g Composition A and 2.0 g of DI Water. Before mixing, sample was heated to 60° C. in an oven. The centrifuge tube was removed and shaken for 30 seconds to mix the layers. Sample was placed back into the oven and monitored for layer separation.

TABLE 1

Water wash data of varying percent water wash

| Layer | Example 9 | | Example 10 | | Example 11 | |
|---|---|---|---|---|---|---|
| | Solvent | Aqueous | Solvent | Aqueous | Solvent | Aqueous |
| H2SO4 (%) | 0.05 | 11.90 | 0.03 | 4.50 | 0.02 | 2.55 |
| LA (%) | 9.90 | 4.45 | 9.43 | 4.70 | 9.15 | 4.62 |
| FA (%) | 1.03 | 4.18 | 0.85 | 3.52 | 0.69 | 2.91 |
| Partition Coefficient (LA) | 2.22 | | 2.01 | | 1.98 | |
| Partition Coefficient (FA) | 0.25 | | 0.24 | | 0.24 | |
| Partition Coefficient (SA) in Water | 17691 | | 75359 | | 213907 | |
| LA/H2SO4 Ratio in Solvent layer | 207.9 | | 320.0 | | 486.7 | |

TABLE 2

Water wash data of varying temperature during separation

| Layer | Example 13(d) | | Example 13(d) | | Example 13(d) | | Example 14 | |
|---|---|---|---|---|---|---|---|---|
| | Solvent | Aqueous | Solvent | Aqueous | Solvent | Aqueous | Solvent | Aqueous |
| H2SO4 (%) | 0.03 | 2.58 | 0.02 | 2.56 | 0.02 | 2.54 | 0.03 | 2.67 |
| LA (%) | 9.19 | 4.34 | 9.19 | 4.35 | 9.10 | 4.38 | 8.95 | 4.30 |
| FA (%) | 0.72 | 3.08 | 0.71 | 3.09 | 0.70 | 3.00 | 0.64 | 2.82 |
| Partition Coefficient (LA) | | 2.12 | | 2.11 | | 2.08 | | 2.08 |
| Partition Coefficient (FA) | | 0.23 | | 0.23 | | 0.23 | | 0.23 |
| Partition Coefficient (SA) in Water | | 154746 | | 166370 | | 149288 | | 121329 |
| LA/H2SO4 Ratio in Solvent layer | | 365.7 | | 396.2 | | 348.4 | | 277.2 |

TABLE 3

Time to maximum separation

| Example | Temperature of Separation (° C.) | Time to Maximum Height of Aqueous Layer (min) |
|---|---|---|
| 12 | 50 | 840 |
| 13(a) | 52 | 840 |
| 14 | 65 | 120 |
| 13(b) | 70 | 120 |
| 13(c) | 80 | 30 |
| 13(d) | 90 | 30 |

In another series of experiments:
Formic acid
Supplier: Alfa Aesar
Purity: 97%
Sulfuric acid
Supplier: Sigma-Aldrich
Purity: 95-98%
Levulinic acid
Supplier: Sigma Aldrich
Purity 98%
LBX-98
Supplier: Merisol
Mixture of 66.9% 2,4 xylenol and 30.6% 2,5 xylenol
Composition B
6.3% levulinic acid
0.73% formic acid
0.58% sulfuric acid
>90% LBX-98

Example 15

A 2 L Erlenmeyer flask was charged with 957 grams of Composition B. By HPLC and titration Composition B extract contained 6.3% levulinic acid, 0.73% formic acid, and 0.58% sulfuric acid. To the flask, 10 grams (1.1 moles NaOH) of 50 wt % sodium hydroxide solution was added. The mixture was mixed well and allowed to sit overnight. Observable solid salts were present on the bottom of the flask the next day. De-ionized water was slowly added while the mixture stirred until the salts had completely dissolved. A total of 58 grams of water was added to the 2 L flask. The extract was separated from the water layer containing the salt by pouring off the organic phase into a new 1 L flask. By HPLC and titration the neutralized extract phase contained 6.0% levulinic acid, 0.69% formic acid and non-detect sulfuric acid.

In still another set of experiments:
Reagents
m-cresol
Supplier: Acros
Purity: 99%
mixed cresol
Supplier: LANXESS
70% m-cresol; 29.5% p-cresol
isoamyl alcohol
Supplier: Sigma Aldrich
Purity: ≥98%
methyl isobutyl carbinol
Supplier: Alfa Aesar
Purity: 99%
2,4-xylenol
Supplier: Alfa Aesar
Purity: 98%
Formic acid
Supplier: Alfa Aesar
Purity: 97%
Sulfuric acid
Supplier: Sigma-Aldrich
Purity: 95-98%
Levulinic acid
Supplier: Sigma Aldrich
Purity 98%

Example 16

(a) An aqueous solution charged with 40% Sulfuric Acid and 8% levulinic acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 16(a) but used mixed cresols as the extraction solvent.

(c) Same as example 16(a) but used isoamyl alcohol as the extraction solvent.

(d) Same as example 16(a) but used methyl isobutyl carbinol as the extraction solvent.

(e) Same as example 16(a) but used 2,4-xylenol as the extraction solvent.

Example 17

(a) An aqueous solution charged with 40% Sulfuric Acid and 2% levulinic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 17(a) but used mixed cresols as the extraction solvent.

(c) Same as example 17(a) but used isoamyl alcohol as the extraction solvent.

(d) Same as example 17(a) but used methyl isobutyl carbinol as the extraction solvent.

(e) Same as example 17(a) but used 2,4-xylenol as the extraction solvent.

Example 18

(a) An aqueous stock solution charged with 40% Sulfuric Acid and 8% Formic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 18(a) but used mixed cresols as the extraction solvent.

(c) Same as example 18(a) but used isoamyl alcohol as the extraction solvent.

(d) Same as example 18(a) but used methyl isobutyl carbinol as the extraction solvent.

(e) Same as example 18(a) but used 2,4-xylenol as the extraction solvent.

Example 19

(a) An aqueous solution charged with 40% Sulfuric Acid and 2% Formic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 19(a) but used mixed cresols as the extraction solvent.

(c) Same as example 19(a) but used isoamyl alcohol as the extraction solvent.

(d) Same as example 19(a) but used 2,4-xylenol as the extraction solvent.

Example 20

(a) An aqueous stock solution charged with 40% Sulfuric Acid, 6% Levulinic Acid and 2% Formic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 20(a) but used mixed cresols as the extraction solvent.

(c) Same as example 20(a) but used isoamyl alcohol as the extraction solvent.

(d) Same as example 20(a) but used methyl isobutyl carbinol as the extraction solvent.

(e) Same as example 20(a) but used 2,4-xylenol as the extraction solvent.

Example 21

(a) An aqueous stock solution charged with 40% Sulfuric Acid, 4% Levulinic Acid and 4% Formic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 21(a) but used mixed cresols as the extraction solvent.

(c) Same as example 21(a) but used isoamyl alcohol as the extraction solvent.

(d) Same as example 21(a) but used methyl isobutyl carbinol as the extraction solvent.

(e) Same as example 21(a) but used 2,4-xylenol as the extraction solvent.

Example 22

(a) An aqueous stock solution charged with 40% Sulfuric Acid, 2% Levulinic Acid and 6% Formic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 22(a) but used mixed cresols as the extraction solvent.

(c) Same as example 22(a) but used isoamyl alcohol as the extraction solvent.

(d) Same as example 22(a) but used methyl isobutyl carbinol as the extraction solvent.

(e) Same as example 22(a) but used 2,4-xylenol as the extraction solvent.

Example 23

(a) An aqueous stock solution charged with 40% Sulfuric Acid, 8% Levulinic Acid and 3% Formic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 23(a) but used mixed cresols as the extraction solvent.

(c) Same as example 23(a) but used isoamyl alcohol as the extraction solvent.

(d) Same as example 23(a) but used methyl isobutyl carbinol as the extraction solvent.

(e) Same as example 23(a) but used 2,4-xylenol as the extraction solvent.

Example 24

(a) An aqueous stock solution charged with 40% Sulfuric Acid and 6% Levulinic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 24(a) but used mixed cresols as the extraction solvent.

(c) Same as example 24(a) but used 2,4-xylenol as the extraction solvent.

Example 25

(a) An aqueous stock solution charged with 40% Sulfuric Acid and 4% Levulinic Acid. A 20 mL centrifuge tube was charged with 5 g of the aqueous solution and 5 g of m-cresol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 25(a) but used mixed cresols as the extraction solvent.

(c) Same as example 25(a) but used 2,4-xylenol as the extraction solvent.

Example 26

(a) Aqueous stock solution charged with 60% Sulfuric Acid, 6% Levulinic Acid and 2% Formic Acid. A 20 mL centrifuge tube was charged with 5 g of the aqueous solution and 5 g of 2,4-xylenol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 26(a) but used 60% Sulfuric Acid, 4% Levulinic Acid, and 4% Formic Acid as the aqueous.

(c) Same as example 26(a) but used 60% Sulfuric Acid, 42% Levulinic Acid, and 6% Formic Acid as the aqueous.

(d) Same as example 26(a) but used 60% Sulfuric Acid, 8% Levulinic Acid, and 3% Formic Acid as the aqueous.

(e) Same as example 26(a) but used 60% Sulfuric Acid and 8% Levulinic Acid as the aqueous.

(f) Same as example 26(a) but used 60% Sulfuric Acid and 6% Levulinic Acid as the aqueous.

(g) Same as example 26(a) but used 60% Sulfuric Acid and 4% Levulinic Acid as the aqueous.

(h) Same as example 26(a) but used 60% Sulfuric Acid and 2% Levulinic Acid as the aqueous.

Example 27

(a) Aqueous stock solution charged with 20% Sulfuric Acid, 6% Levulinic Acid and 2% Formic Acid. A 20 mL centrifuge tube was charged with 5 g of the aqueous solution and 5 g of 2,4-xylenol as the extraction solvent. Centrifuge tube was shaken for 30 seconds to thoroughly mix the layers. Centrifuge tube was centrifuged for 15 minutes to separate the layers. Sample layers were separated via pipette into scintillation vials.

(b) Same as example 27(a) but used 20% Sulfuric Acid, 4% Levulinic Acid, and 4% Formic Acid as the aqueous.

(c) Same as example 27(a) but used 20% Sulfuric Acid, 42% Levulinic Acid, and 6% Formic Acid as the aqueous.

(d) Same as example 27(a) but used 20% Sulfuric Acid, 8% Levulinic Acid, and 3% Formic Acid as the aqueous.

(e) Same as example 27(a) but used 20% Sulfuric Acid and 8% Levulinic Acid as the aqueous.

(f) Same as example 27(a) but used 20% Sulfuric Acid and 6% Levulinic Acid as the aqueous.

(g) Same as example 27(a) but used 20% Sulfuric Acid and 4% Levulinic Acid as the aqueous.

(h) Same as example 27(a) but used 20% Sulfuric Acid and 2% Levulinic Acid as the aqueous.

TABLE 4

| Layer | Example 16(a) | | Example 16(b) | | Example 16(c) | | Example 16(d) | | Example 16(e) | |
|---|---|---|---|---|---|---|---|---|---|---|
| | Solvent | Aqueous | Solvent | Aqueous | Solvent | Aqueous | Solvent | Aqueous | Solvent | Aqueous |
| LA (%) | 6.96 | 1.76 | 7.21 | 1.85 | 0.65 | 1.83 | 0.85 | 4.36 | 6.57 | 2.03 |
| Partition Coefficient (LA) | 3.95 | | 3.90 | | 0.36 | | 0.19 | | 3.24 | |

TABLE 5

| Layer | Example 17(a) | | Example 17(b) | | Example 17(c) | | Example 17(d) | | Example 17(e) | |
|---|---|---|---|---|---|---|---|---|---|---|
| | Solvent | Aqueous | Solvent | Aqueous | Solvent | Aqueous | Solvent | Aqueous | Solvent | Aqueous |
| LA (%) | 1.90 | 0.41 | 1.92 | 0.40 | 0.19 | 0.65 | 0.30 | 1.04 | 1.81 | 0.49 |
| Partition Coefficient (LA) | 4.63 | | 4.80 | | 0.29 | | 0.29 | | 3.69 | |

TABLE 6

| Layer | Example 18(a) | | Example 18(b) | | Example 18(c) | | Example 18(d) | | Example 18(e) | |
|---|---|---|---|---|---|---|---|---|---|---|
| | Solvent | Aqueous | Solvent | Aqueous | Solvent | Aqueous | Solvent | Aqueous | Solvent | Aqueous |
| FA (%) | 2.47 | 7.35 | 2.5 | 7.23 | 5.24 | 0.84 | 1.76 | 1.16 | 1.86 | 7.53 |
| Partition Coefficient (FA) | 0.34 | | 0.35 | | 6.24 | | 1.52 | | 0.25 | |

TABLE 7

| Layer | Example 19(a) | | Example 19(b) | | Example 19(c) | | Example 19(d) | |
|---|---|---|---|---|---|---|---|---|
| | Solvent | Aqueous | Solvent | Aqueous | Solvent | Aqueous | Solvent | Aqueous |
| FA (%) | 0.62 | 1.87 | 0.62 | 1.87 | 1.27 | 0.36 | 0.95 | 0.89 |
| Partition Coefficient (FA) | 0.33 | | 0.33 | | 3.53 | | 1.07 | |

TABLE 8

| Layer | Example 20(a) | | Example 20(b) | | Example 20(c) | | Example 20(d) | | Example 20(e) | |
|---|---|---|---|---|---|---|---|---|---|---|
| | Solvent | Aqueous | Solvent | Aqueous | Solvent | Aqueous | Solvent | Aqueous | Solvent | Aqueous |
| LA (%) | 4.47 | 1.28 | 4.95 | 1.3 | 0.5 | 1.66 | 0.87 | 2.95 | 4.790 | 1.540 |
| FA (%) | 0.65 | 1.88 | 0.65 | 1.88 | 1.31 | 0.18 | 0.73 | 0.34 | 0.540 | 1.930 |
| Partition Coefficient (LA) | 3.49 | | 3.81 | | 0.30 | | 0.29 | | 3.11 | |
| Partition Coefficient (FA) | 0.35 | | 0.35 | | 7.28 | | 2.15 | | 0.28 | |

TABLE 9

| Layer | Example 21(a) | | Example 21(b) | | Example 21(c) | | Example 21(d) | | Example 21(e) | |
|---|---|---|---|---|---|---|---|---|---|---|
| | Solvent | Aqueous | Solvent | Aqueous | Solvent | Aqueous | Solvent | Aqueous | Solvent | Aqueous |
| LA (%) | 3.66 | 0.86 | 3.36 | 0.84 | 0.37 | 1.19 | 1.05 | 1.88 | 3.280 | 1.010 |
| FA (%) | 1.31 | 3.55 | 1.24 | 3.54 | 2.75 | 0.37 | 1.3 | 0.62 | 1.050 | 3.650 |
| Partition Coefficient (LA) | 4.26 | | 4.00 | | 0.31 | | 0.56 | | 3.25 | |
| Partition Coefficient (FA) | 0.37 | | 0.35 | | 7.43 | | 2.10 | | 0.29 | |

TABLE 10

| Layer | Example 22(a) | | Example 22(b) | | Example 22(c) | | Example 22(d) | | Example 22(e) | |
|---|---|---|---|---|---|---|---|---|---|---|
| | Solvent | Aqueous | Solvent | Aqueous | Solvent | Aqueous | Solvent | Aqueous | Solvent | Aqueous |
| LA (%) | 2 | 0.46 | 1.73 | 0.44 | 0.24 | 0.67 | 1.25 | 1.1 | 1.650 | 0.530 |
| FA (%) | 1.87 | 5.16 | 1.86 | 5.16 | 4.19 | 0.55 | 1.98 | 0.88 | 1.500 | 5.310 |
| Partition Coefficient (LA) | 4.35 | | 3.93 | | 0.36 | | 1.14 | | 3.11 | |
| Partition Coefficient (FA) | 0.36 | | 0.36 | | 7.62 | | 2.25 | | 0.28 | |

TABLE 11

| Layer | Example 23(a) | | Example 23(b) | | Example 23(c) | | Example 23(d) | | Example 23(e) | |
|---|---|---|---|---|---|---|---|---|---|---|
| | Solvent | Aqueous | Solvent | Aqueous | Solvent | Aqueous | Solvent | Aqueous | Solvent | Aqueous |
| LA (%) | 6.35 | 1.79 | 6.33 | 1.78 | 0.63 | 2.29 | 1.17 | 3.9 | 5.980 | 2.140 |
| FA (%) | 0.9 | 2.61 | 0.91 | 2.68 | 1.83 | 0.25 | 0.95 | 0.42 | 0.780 | 2.710 |
| Partition Coefficient (LA) | 3.55 | | 3.56 | | 0.28 | | 0.30 | | 2.79 | |
| Partition Coefficient (FA) | 0.34 | | 0.34 | | 7.32 | | 2.26 | | 0.29 | |

TABLE 12

| Layer | Example 24(a) | | Example 24(b) | | Example 24(c) | |
|---|---|---|---|---|---|---|
| | Solvent | Aqueous | Solvent | Aqueous | Solvent | Aqueous |
| LA (%) | 4.91 | 1.14 | 5.03 | 1.14 | 3.921 | 1.704 |
| Partition Coefficient (LA) | 4.31 | | 4.41 | | 2.30 | |

TABLE 13

| Layer | Example 25(a) | | Example 25(b) | | Example 25(c) | |
|---|---|---|---|---|---|---|
| | Solvent | Aqueous | Solvent | Aqueous | Solvent | Aqueous |
| LA (%) | 2.93 | 0.70 | 3.27 | 0.71 | 2.63 | 1.08 |
| Partition Coefficient (LA) | 4.19 | | 4.61 | | 2.43 | |

TABLE 14

| Layer | Example 26(a) | | Example 26(b) | | Example 26(c) | | Example 26(d) | |
|---|---|---|---|---|---|---|---|---|
| | Solvent | Aqueous | Solvent | Aqueous | Solvent | Aqueous | Solvent | Aqueous |
| H2SO4 (%) | 0.688 | N/D | 0.629 | N/D | 0.628 | N/D | 1.261 | N/D |
| LA (%) | 2.426 | 3.467 | 1.616 | 2.362 | 0.645 | 1.531 | 2.273 | 6.461 |
| FA (%) | 0.344 | 1.672 | 0.690 | 3.323 | 0.763 | 6.350 | 0.406 | 3.328 |
| Partition Coefficient (LA) | 0.70 | | 0.68 | | 0.42 | | 0.35 | |
| Partition Coefficient (FA) | 0.21 | | 0.21 | | 0.12 | | 0.12 | |

N/D = not determined

TABLE 15

| Layer | Example 26(e) | | Example 26(f) | | Example 26(g) | | Example 26(h) | |
|---|---|---|---|---|---|---|---|---|
| | Solvent | Aqueous | Solvent | Aqueous | Solvent | Aqueous | Solvent | Aqueous |
| H2SO4 (%) | 0.727 | N/D | 0.562 | N/D | 0.490 | N/D | 0.368 | N/D |
| LA (%) | 2.524 | 5.958 | 2.075 | 4.082 | 1.456 | 2.540 | 0.747 | 1.202 |
| Partition Coefficient (LA) | 0.42 | | 0.51 | | 0.57 | | 0.62 | |

N/D = not determined

TABLE 16

| Layer | Example 27(a) | | Example 27(b) | | Example 27(c) | | Example 27(d) | |
|---|---|---|---|---|---|---|---|---|
| | Solvent | Aqueous | Solvent | Aqueous | Solvent | Aqueous | Solvent | Aqueous |
| H2SO4 (%) | N/D | N/D | 0.097 | N/D | 0.017 | N/D | 0.025 | N/D |
| LA (%) | 5.573 | 1.051 | 3.789 | 0.718 | 1.543 | 0.462 | 5.682 | 1.695 |
| FA (%) | 0.055 | 1.886 | 1.039 | 3.758 | 1.167 | 7.095 | 0.062 | 3.719 |
| Partition Coefficient (LA) | 5.30 | | 5.28 | | 3.34 | | 3.35 | |
| Partition Coefficient (FA) | 0.03 | | 0.28 | | 0.16 | | 0.02 | |

N/D = not determined

TABLE 17

| Layer | Example 27(e) | | Example 27(f) | | Example 27(g) | | Example 27(h) | |
|---|---|---|---|---|---|---|---|---|
| | Solvent | Aqueous | Solvent | Aqueous | Solvent | Aqueous | Solvent | Aqueous |
| H2SO4 (%) | 0.019 | N/D | 0.254 | N/D | 0.111 | N/D | 0.010 | N/D |
| LA (%) | 5.978 | 1.650 | 4.553 | 1.227 | 3.016 | 0.814 | 1.494 | 0.401 |
| Partition Coefficient (LA) | 3.62 | | 3.71 | | 3.71 | | 3.72 | |

N/D = not determined

In still more examples:

Example 28

Into a 1 L four neck round bottom flask containing a magnetic stir bar charged 171.23 g DI water, 357.85 g (2.34 mol) sulfuric acid (64%) and 3.01 g m-Cresol. The round bottom flask was situated in a heating mantle and equipped with a thermocouple, condenser, glass stopper, and a syringe pump inlet. The water, sulfuric acid and cresol mixture was heated to 90° C. while stirring at 500 RPM. Into a 60 mL syringe charged 59.02 g (42 mL) Cornsweet 90. (Corn Sweet 90 is a high-fructose syrup (90% fructose, 8.5% glucose, 1.5% oligiomeric sugars) supplied by Archer Daniels Midland (ADM). It contains 77% solids.)

Once the sulfuric acid, water and cresol mixture reached a temperature of 90° C. the cornsweet 90 started to be added to the mixture via a syringe pump at a rate of 16.8 mL/hr. After 2.5 hours, all of the cornsweet 90 had been added to the round bottom flask and the reaction mixture was left to react for an additional hour. After a total reaction time of 3.5 hours the heat was turned off and the reaction mixture was allowed to cool to ambient temperature. Once the reaction mixture was cool it was filtered through a 1.1 μm glass microfiber filter. The char was then washed with methanol and DI water and measured using a moisture analyzer. Samples were pulled throughout the reaction and analyzed by HPLC.

Reaction observations: After 60 minutes of reaction time there appeared to be a plastic looking film on the surface of the reaction mixture and the mixture itself looked thick. It was not apparent whether or not the magnetic stir bar was still stirring. Once the reaction was filtered it was very clear that the magnetic stir bar had indeed stopped stirring because it was completely encased by a very hard solid substance which had stuck to the bottom of the round bottom flask. The char formed clumps and seemed to have some shiny attributes to it.

| Sample | Time (min) | % Glucose | % Fructose | % FA | % LA | % HMF | % Cresol |
|---|---|---|---|---|---|---|---|
| Example 28 | 210 | 0.86 | 0.00 | 1.22 | 2.71 | 0.01 | 0.00 |

| | |
|---|---|
| LA Molar % Yield | 57.68 |
| FA Molar % Yield | 65.50 |
| LA to Char Ratio | 1.95 |

Example 29

Into a 1 L four neck round bottom flask containing a magnetic stir bar charged 171.61 g DI water, 357.81 g (2.33 mol) sulfuric acid (64%) and 9244 (7.7 mmol) 2,4-Xylenol. The round bottom flask was situated in a heating mantle and equipped with a thermocouple, condenser, glass stopper, and a syringe pump inlet. The water, sulfuric acid and xylenol mixture was heated to 90° C. while stirring at 500 RPM. Into a 60 mL syringe charged 59.03 g (43 mL) cornsweet 90. Once the sulfuric acid, water and xylenol mixture reached a temperature of 90° C. the cornsweet 90 started to be added to the mixture via a syringe pump at a rate of 17.2 mL/hr. After 2.5 hours, all of the cornsweet 90 had been added to the round bottom flask and the reaction mixture was left to react for an additional hour. After a total reaction time of 3.5 hours the heat was turned off and the reaction mixture was allowed to cool to ambient temperature. Once the reaction mixture was cool it was filtered through a 1.1 μm glass microfiber filter. The char was then washed with DI water and measured using a moisture analyzer. Samples were pulled throughout the reaction and analyzed by HPLC.

Reaction Observations: After 40 minutes of reaction time there was a plastic looking film on the surface of the reaction mixture and the reaction mixture looked thick. It was not apparent whether or not the magnetic stir bar was still stirring. A foam ball had formed in the center of the flask and when a spatula was used to try to break up the char it was unsuccessful because the char was so hard. Once the reaction mixture was filtered and all of the liquid had been poured out of the round bottom flask it was very clear that the magnetic stir bar had stopped stirring because it was completely encased by a very hard char substance which also covered the entire bottom of the flask. The char formed clumps and seemed to have some shiny attributes to it.

| Sample | Time (min) | % Glucose | % Fructose | % FA | % LA | % HMF | % Xylenol |
|---|---|---|---|---|---|---|---|
| Example 29A | 20 | 0.08 | 0.34 | 0.00 | 0.05 | 0.08 | 0.04 |
| Example 29B | 210 | 0.80 | 0.00 | 1.19 | 2.73 | 0.00 | 0.00 |

| | |
|---|---|
| LA Molar % Yield | 58.05 |
| FA Molar % Yield | 64.02 |
| LA to Char Ratio | 1.94 |

Example 30

Into a 1 L four neck round bottom flask containing a magnetic stir bar charged 171.21 g DI water, 357.85 g (2.34 mol) sulfuric acid (64%) and 5784 (4.8 mmol) 2,4-Xylenol. The round bottom flask was situated in a heating mantle and equipped with a thermocouple, condenser, glass stopper, and a syringe pump inlet. The water, sulfuric acid and xylenol mixture was heated to 90° C. while stirring at 500 RPM. Into a 60 mL syringe charged 59.02 g (43 mL) cornsweet 90.

Once the sulfuric acid, water and xylenol mixture reached a temperature of 90° C. the cornsweet 90 started to be added to the mixture via a syringe pump at a rate of 17.2 mL/hr. After 2.5 hours, all of the cornsweet 90 had been added to the round bottom flask and the reaction mixture was left to react for an additional hour. After a total reaction time of 3.5 hours the heat was turned off and the reaction mixture was allowed to cool to ambient temperature. Once the reaction mixture was cool it was filtered through a 1.1 μm glass microfiber filter. The char was then washed with DI water and measured using a moisture analyzer. Samples were pulled throughout the reaction and analyzed by HPLC.

Reaction Observations: After 40 minutes of reaction time, it was apparent that the magnetic stir bar had stopped stirring but it was able to be dislodged from the bottom of the flask by poking with the Teflon coated thermocouple. The char had to be broken up again after 120 minutes of reaction time. When the reaction mixture was filtered and all of the liquid had been poured out of the flask, there was not much char stuck to the reactor. There was char stuck to the magnetic stir bar and it was hard.

| Sample | Time (min) | % Glucose | % Fructose | % FA | % LA | % HMF |
|---|---|---|---|---|---|---|
| Example 30 | 210 | 0.81 | 0.00 | 1.20 | 2.91 | 0.00 |

| | |
|---|---|
| LA Molar % Yield | 64.60 |
| FA Molar % Yield | 68.16 |
| LA to Char Ratio | 2.51 |

Example 31

Into a 1 L four neck round bottom flask containing a magnetic stir bar charged 171.30 g DI water, 357.87 g (2.34 mol) sulfuric acid (64%) and 462.104 (3.9 mmol) 2,4-Xylenol. The round bottom flask was situated in a heating mantle and equipped with a thermocouple, condenser, glass stopper, and a syringe pump inlet. The water, sulfuric acid and xylenol mixture was heated to 90° C. while stirring at 500 RPM. Into a 60 mL syringe charged 58.98 g (43 mL) cornsweet 90. Once the sulfuric acid, water and xylenol mixture reached a temperature of 90° C. the cornsweet 90 started to be added to the mixture via a syringe pump at a rate of 17.2 mL/hr. After 2.5 hours, all of the cornsweet 90 had been added to the round bottom flask and the reaction mixture was left to react for an additional hour. After a total reaction time of 3.5 hours the heat was turned off and the reaction mixture was allowed to cool to ambient temperature. Once the reaction mixture was cool it was filtered through a 1.1 μm glass microfiber filter. The char was then washed with DI water and measured using a moisture analyzer. Samples were pulled throughout the reaction and analyzed by HPLC.

Reaction Observations: After 40 minutes of reaction time, it was apparent that the magnetic stir bar had stopped stirring but it was able to be dislodged from the bottom of the flask by poking with the Teflon coated thermocouple. When the reaction mixture was filtered and all of the liquid had been poured out of the flask, there was not much char stuck to the glass but there was some very hard char stuck to the magnetic stir bar.

| Sample | Time (min) | % Glucose | % Fructose | % FA | % LA | % HMF |
|---|---|---|---|---|---|---|
| Example 31 | 210 | 0.81 | 0.00 | 1.20 | 2.92 | 0.00 |

| | |
|---|---|
| LA Molar % Yield | 64.04 |
| FA Molar % Yield | 66.80 |
| LA to Char Ratio | 2.55 |

Example 32

Into a 1 L four neck round bottom flask containing a magnetic stir bar charged 171.21 g DI water, 357.89 g (2.34 mol) sulfuric acid (64%) and 231.044 (1.9 mmol) 2,4-Xylenol. The round bottom flask was situated in a heating mantle and equipped with a thermocouple, condenser, glass stopper, and a syringe pump inlet. The water, sulfuric acid and xylenol mixture was heated to 90° C. while stirring at 500 RPM. Into a 60 mL syringe charged 58.99 g (43 mL) cornsweet 90. Once the sulfuric acid, water and xylenol mixture reached a temperature of 90° C. the cornsweet 90 started to be added to the mixture via a syringe pump at a rate of 17.2 mL/hr. After 2.5 hours, all of the cornsweet 90 had been added to the round bottom flask and the reaction mixture was left to react for an additional hour. After a total reaction time of 3.5 hours the heat was turned off and the reaction mixture was allowed to cool to ambient temperature. Once the reaction mixture was cool it was filtered through a 1.1 μm glass microfiber filter. The char was then washed with DI water and measured using a moisture analyzer. Samples were pulled throughout the reaction and analyzed by HPLC.

Reaction Observations: When the magnetic stir bar was removed from the flask at the end of the reaction there were some small spots of hard char visibly stuck to the magnetic stir bar. When all of the liquid had been poured out of the flask there was a ring of char that was left but it was easily removed when squirted with DI water.

| Sample | Time (min) | % Glucose | % Fructose | % FA | % LA | % HMF | % Xylenol |
|---|---|---|---|---|---|---|---|
| Example 32 | 210 | 0.81 | 0.00 | 1.22 | 3.05 | 0.00 | 0.00 |

| | |
|---|---|
| LA Molar % Yield | 66.12 |
| FA Molar % Yield | 66.80 |
| LA to Char Ratio | 2.75 |

Example 33

Into a 1 L four neck round bottom flask containing a magnetic stir bar charged 171.21 g DI water, 357.85 g (2.34 mol) sulfuric acid (64%) and 28.884 (0.24 mmol) 2,4-Xylenol. The round bottom flask was situated in a heating mantle and equipped with a thermocouple, condenser, glass stopper, and a syringe pump inlet. The water, sulfuric acid and xylenol mixture was heated to 90° C. while stirring at 500 RPM. Into a 60 mL syringe charged 59.02 g (43 mL) cornsweet 90. Once the sulfuric acid, water and xylenol mixture reached a temperature of 90° C. the cornsweet 90 started to be added to the mixture via a syringe pump at a rate of 17.2 mL/hr. After 2.5 hours, all of the cornsweet 90 had been added to the round bottom flask and the reaction mixture was left to react for an additional hour. After a total reaction time of 3.5 hours the heat was turned off and the reaction mixture was allowed to cool to ambient temperature. Once the reaction mixture was cool it was filtered through a 1.1 μm glass microfiber filter. The char was then washed with DI water and measured using a moisture analyzer. Samples were pulled throughout the reaction and analyzed by HPLC.

Reaction Observations: There were no problems stirring the reaction mixture since the char was well dispersed and did not form clumps. This char had similar characteristics as to what is normally observed in a fructose hydrolysis reaction to LA using these reaction conditions.

| Sample | Time (min) | % Glucose | % Fructose | % FA | % LA | % HMF | % Xylenol |
|---|---|---|---|---|---|---|---|
| Example 33 | 210 | 0.82 | 0.00 | 1.23 | 2.96 | 0.00 | 0.00 |

| | |
|---|---|
| LA Molar % Yield | 68.00 |
| FA Molar % Yield | 72.63 |
| LA to Char Ratio | 2.85 |

Example 34

Into a 1 L four neck round bottom flask containing a magnetic stir bar charged 171.24 g DI water, 357.88 g (2.34 mol) sulfuric acid (64%) and 11.554 (0.10 mmol) 2,4-Xylenol. The round bottom flask was situated in a heating mantle and equipped with a thermocouple, condenser, glass stopper, and a syringe pump inlet. The water, sulfuric acid and xylenol mixture was heated to 90° C. while stirring at 500 RPM. Into a 60 mL syringe charged 58.99 g (43 mL) cornsweet 90. Once the sulfuric acid, water and xylenol mixture reached a temperature of 90° C. the cornsweet 90 started to be added to the mixture via a syringe pump at a rate of 17.2 mL/hr. After 2.5 hours, all of the cornsweet 90 had been added to the round bottom flask and the reaction mixture was left to react for an additional hour. After a total reaction time of 3.5 hours the heat was turned off and the reaction mixture was allowed to cool to ambient temperature. Once the reaction mixture was cool it was filtered through a 1.1 μm glass microfiber filter. The char was then washed with DI water and measured using a moisture analyzer. Samples were pulled throughout the reaction and analyzed by HPLC.

Reaction observations: There were no problems stirring the reaction mixture since the char was well dispersed and did not form clumps. This char had similar characteristics as to what is normally observed in a fructose hydrolysis using these reaction conditions.

| Sample | Time (min) | % Glucose | % Fructose | % FA | % LA | % HMF |
|---|---|---|---|---|---|---|
| Example 34 | 210 | 0.81 | 0.00 | 1.22 | 3.02 | 0.00 |

| | |
|---|---|
| LA Molar % Yield | 67.94 |
| FA Molar % Yield | 69.82 |
| LA to Char Ratio | 2.81 |

Example 35

Into a 1 L four neck round bottom flask containing a magnetic stir bar charged 171.18 g DI water, 357.91 g (2.34 mol) sulfuric acid (64%) and 9244 (7.7 mmol) 2,4-Xylenol. The round bottom flask was situated in a heating mantle and equipped with a thermocouple, condenser, and two glass stoppers. The water, sulfuric acid and xylenol mixture was heated to 110° C. while stirring at 500 RPM to get the mixture to reflux. After refluxing for 125 minutes the heat was turned off and the mixture was allowed to cool to ambient temperature. Once the mixture was cool it was filtered through a 1.1 μm glass microfiber filter. A sample of the filtered mixture was taken and analyzed by HPLC which indicated that there was still 0.13% xylenol after the heat treatment. The heat treatment step did not effectively remove xylenol to a low level.

Example 36

5 wt % activated carbon was added to the mixture from Example 35, and the mixture was stirred at ambient temperature for 185 minutes. Samples were pulled after 100 and 185 minutes. The heat was then turned on to heat up the mixture to 68.7° C. and once the mixture reached that temperature another sample was taken. The samples were analyzed by HPLC for Xylenol. The first sample that was pulled after 100 minutes and mixing at ambient temperature showed that all of the xylenol had been removed (non-detect by HPLC). All of the activated carbon was filtered out of the mixture using a 1.1 μm glass microfiber filter. The filtered mixture was then charged into a clean 1 L four neck round bottom flask and equipped with a thermocouple, condenser, glass stopper, and a syringe pump inlet. The water and sulfuric acid mixture was heated to 90° C. while stirring at 500 RPM. Into a 60 mL syringe charged 58.98 g (43 mL) cornsweet 90. Once the sulfuric acid and water mixture reached a temperature of 90° C. the cornsweet 90 started to be added to the mixture via a syringe pump at a rate of 17.2 mL/hr. After 2.5 hours, all of the cornsweet 90 had been added to the round bottom flask and the reaction mixture was left to react for an additional hour. After a total reaction time of 3.5 hours the heat was turned off and the reaction mixture was allowed to cool to ambient temperature. Once the reaction mixture was cool it was filtered through a 1.1 μm glass microfiber filter. The char was then washed with DI water and measured using a moisture analyzer. Samples were pulled throughout the reaction and analyzed by HPLC.

Reaction Observations: There were no problems stirring the reaction mixture since the char was well dispersed and did not form clumps. This char had similar characteristics as to what is normally observed in a fructose hydrolysate under these conditions.

| Sample | Time (min) | % Glucose | % Fructose | % FA | % LA | % HMF |
|---|---|---|---|---|---|---|
| Example 36 | 210 | 0.94 | 0.00 | 1.43 | 3.41 | 0.00 |

| | |
|---|---|
| LA Molar % Yield | 76.81 |
| FA Molar % Yield | 82.33 |
| LA to Char Ratio | 3.09 |

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A process to prepare levulinic acid comprising the steps:
   a) heating an aqueous solution of a mineral acid to a temperature from about 60° C. to about 160° C. in a reactor, wherein the mineral acid is present from at least 20 percent by weight to about 80 percent by weight; and
   b) adding a monosaccharide or di-saccharide to the heated aqueous acid in the reactor to form a reaction mixture at a rate such that the monosaccharide content of the reaction mixture remains less than or equal to about 5% by weight of the reaction mixture during the entire reaction, to provide levulinic acid.

2. The process of claim 1, further comprising the step of combining the reaction mixture comprising levulinic acid with a phenolic or substituted phenolic extraction solvent to create an extraction phase and an aqueous raffinate phase, wherein levulinic acid and optionally, formic acid are in the extraction phase.

3. The process of claim 2, wherein the phenolic or substituted phenolic extraction solvent is a phenol, an alkylphenol, a xylenol, a methoxyphenol, a cresol, a polydimethylsiloxane, a substituted alkyl phenol, a tertiary amine/alkyl phenol mixture, phenol/alkyl phenol blends with a C5-C36 hydrocarbon or C6-C12 aromatic hydrocarbons, 2-ethyl-hexanoic acid or perfluoro-octanoic acid or perfluoro-octanol or mixtures thereof.

4. The process of claim 3, wherein the extraction solvent comprises phenol, 4-methoxyphenol, 2-methoxyphenol, 3-methoxyphenol, 2-sec-butyl phenol, 3-sec-butyl phenol, 4-sec-butyl phenol, 2-t-butyl phenol, 4-t-butyl phenol, 2,4-di-t-butyl phenol, 2,4-di-methoxyphenol, 2-methylphenol, 3-methylphenol, 4-methylphenol, 2,3-xylenol, 2, 4-xylenol, 2, 5-xylenol, 2, 6-xylenol, 3, 4-xylenol, or 3, 5-xylenol, 4-hexyl-resorcinol, butylated hydroxyl-toluene (BHT), 2,5-dimethoxyphenol, 3,5-dimethoxy phenol, 2,6-dimethoxy phenol, nonylphenol, or mixtures thereof.

5. The process of claim 2, further comprising the step of subjecting the extraction phase to a base, an anion exchange resin, or water washing the extraction phase to reduce the amount of mineral acid present to less than or equal to 0.5 weight percent of the extraction phase.

6. The process of claim 2, further comprising the step of treating the aqueous raffinate phase with an adsorbent, such as activated carbon or with a hydrocarbon solvent to decrease the amount of the extraction solvent from the raffinate phase.

7. A process to prepare levulinic acid comprising the steps:
   a) providing a heated reaction mixture comprising a biomass, water and a mineral acid, at a temperature from about 60° C. to about 160° C., such that the monosaccharide content of the reaction mixture remains less than or equal to about 5% by weight of the reaction mixture during the entire reaction, to produce levulinic acid;
   b) extracting levulinic acid from the reaction mixture with an extraction solvent in an extraction system, wherein the extracted levulinic acid and extraction solvent comprise an extraction phase;
   c) recycling an aqueous raffinate recycle stream from the extraction vessel to the reactor wherein the recycle stream comprises the water, the mineral acid and less than or equal to 0.5 weight percent of the extraction solvent; and
   d) distilling the extraction solvent such that the extraction solvent contains <1% mineral acid prior to recycling back to the extraction system.

8. The process of claim 7, wherein the extraction solvent is a phenolic or substituted phenolic comprising phenol, an alkylphenol, a xylenol, a methoxyphenol, a cresol, a polydimethylsiloxane, a substituted alkyl phenol, a tertiary amine/alkyl phenol mixture, phenol/alkyl phenol blends with a C5-C36 hydrocarbon or C6-C12 aromatic hydrocarbons, 2-ethyl-hexanoic acid or perfluoro-octanoic acid or perfluoro-octanol or mixtures thereof.

9. The process of claim 8, wherein the extraction solvent comprises phenol, 4-methoxyphenol, 2-methoxyphenol, 3-methoxyphenol, 2-sec-butyl phenol, 3-sec-butyl phenol, 4-sec-butyl phenol, 2-t-butyl phenol, 4-t-butyl phenol, 2,4-di-t-butyl phenol, 2,4-di-methoxyphenol, 2-methylphenol, 3-methylphenol, 4-methylphenol, 2,3-xylenol, 2, 4-xylenol, 2, 5-xylenol, 2, 6-xylenol, 3, 4-xylenol, or 3, 5-xylenol, 4-hexyl-resorcinol, butylated hydroxyl-toluene (BHT), 2,5-dimethoxyphenol, 3,5-dimethoxy phenol, 2,6-dimethoxy phenol, nonylphenol, or mixtures thereof.

10. The process of claim 7, further comprising the step of subjecting the extraction phase to a base, an anion exchange resin, or water washing the extraction phase to reduce the amount of mineral acid present to less than or equal to 0.5 weight percent of the extraction phase.

11. The process of claim 7, further comprising the step of treating the aqueous raffinate phase with an adsorbent, such as activated carbon or with a hydrocarbon solvent to decrease the amount of the extraction solvent from the raffinate phase.

12. The process of claim 7, further comprising the step of washing char/solids with water to form a filtrate and combining the filtrate with the raffinate or contacting the filtrate with an extraction solvent.

13. The process of claim 7, further comprising the step of recycling the extraction phase to a liquid extraction system.

14. The process of claim 7, wherein step (a) is conducted in a batch.

15. The process of claim 7, wherein the recycle step is conducted in a continuous manner.

16. The process of claim 7, wherein the distillation step is conducted in a continuous manner.

* * * * *